(12) United States Patent
Balschat et al.

(10) Patent No.: US 8,104,348 B2
(45) Date of Patent: Jan. 31, 2012

(54) METHOD AND DEVICE FOR MONITORING A FLOWING LIQUID FOR THE PRESENCE OF AIR

(75) Inventors: Klaus Balschat, Schwebheim (DE); Tobias Fritsche, Halle (DE); Alfred Gagel, Litzendorf (DE); Steffen Kirchner, Schweinfurt (DE); Hans-Joachim Muench, Halle (DE); Olaf Nicholas, Kiteingen (DE); Jochen Schneider, Wipfeld (DE); Reiner Spickermann, Wasserlosen-Burghausen (DE); Santer Zur Host-Meyer, Halle (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 758 days.

(21) Appl. No.: 11/921,624

(22) PCT Filed: Apr. 15, 2006

(86) PCT No.: PCT/EP2006/003484
§ 371 (c)(1),
(2), (4) Date: Jun. 6, 2008

(87) PCT Pub. No.: WO2006/128520
PCT Pub. Date: Dec. 7, 2006

(65) Prior Publication Data
US 2009/0205426 A1    Aug. 20, 2009

(30) Foreign Application Priority Data
Jun. 3, 2005   (DE) .......................... 10 2005 025 515

(51) Int. Cl.
*G01H 3/12* (2006.01)
(52) U.S. Cl. ........................................ 73/599
(58) Field of Classification Search .................... 73/599, 73/649
See application file for complete search history.

(56) References Cited

U.S. PATENT DOCUMENTS
4,651,555 A    3/1987   Dam ............................. 73/19.03
(Continued)

FOREIGN PATENT DOCUMENTS
DE           40 13 402         11/1991
(Continued)

OTHER PUBLICATIONS
International Search Report for PCT/EP2006/003484.
(Continued)

*Primary Examiner* — Hezron E Williams
*Assistant Examiner* — Tamiko Bellamy
(74) *Attorney, Agent, or Firm* — Kenyon & Kenyon LLP

(57) ABSTRACT

The present invention relates to a method and a device for monitoring a flowing medium, in particular the blood flowing in an extracorporeal blood circulation, for the presence of air, in particular micro-bubbles. A sequence of signal pulses or a continuous signal is injected into the flowing medium, and the signal pulses or continuous signal leaving the flowing medium are received. To detect micro-bubbles, a signal pattern that is characteristic of the variation over time of the received signal pulses or the continuous signal in a predetermined period of time is extracted from the signal received. The characteristic signal pattern is compared with one or more characteristic reference patterns, and the presence of air bubbles is determined if the characteristic signal pattern deviates from the characteristic reference pattern by a predetermined amount. Statistical characteristic variables, in particular the variance, are preferably determined from the signal patterns and compared with one another.

16 Claims, 3 Drawing Sheets

U.S. PATENT DOCUMENTS

| | | | | |
|---|---|---|---|---|
| 5,394,732 | A | 3/1995 | Johnson et al. | 73/19.1 |
| 5,824,881 | A | 10/1998 | Shouldice et al. | 73/19.1 |
| 2004/0154374 | A1 | 8/2004 | Daw et al. | 73/1.02 |

FOREIGN PATENT DOCUMENTS

| | | |
|---|---|---|
| EP | 0643301 | 9/1994 |
| EP | 1182452 | 2/2002 |
| JP | 10216227 A * | 8/1998 |

OTHER PUBLICATIONS

English translation of the International Preliminary Report on Patentability for PCT/EP2006/003484.

Droste, D.W., Kuhne, K., Schaefer, R.M., Ringelstein, E.B., "Detection of microemboli in the subclavian vein of patients undergoing haemodialysis and haemodiafiltration using pulsed Doppler ultrasound", Nephrol. Dial. Transplant 2002; 17: 462-466.

* cited by examiner

METHOD AND DEVICE FOR MONITORING A FLOWING LIQUID FOR THE PRESENCE OF AIR

FIELD OF THE INVENTION

The present invention relates to a method of monitoring a flowing liquid, and in particular the blood flowing in an extra-corporeal blood circulatory system of an extra-corporeal blood treating apparatus, for the presence of air, and to a method for the extra-corporeal treatment of blood using an extra-corporeal blood circulatory system in which the presence of air in the extra-corporeal blood circulatory system is monitored for. The present invention also relates to an arrangement for monitoring a flowing liquid, and in particular the blood flowing in an extra-corporeal blood circulatory system, for the presence of air, and to an apparatus for the extra-corporeal treatment of blood having an arrangement for monitoring the blood flowing in the extra-corporeal blood circulatory system of the treating apparatus for the presence of air.

BACKGROUND OF THE INVENTION

Various methods are known for the extra-corporeal treatment of blood in which the patient's blood flows through a blood treating unit in an extra-corporeal blood circulatory system. One of the chief complications of the extra-corporeal treatment of blood, such as hemodialysis or hemofiltration, is the possibility of air penetrating into the extra-corporeal blood circulatory system. The same risk exists not only with extra-corporeal treatments of blood but also with infusions using infusion solutions.

To separate entrained air bubbles from blood and infusion solutions, known drip chambers are arranged in the venous segment of the extra-corporeal circulatory system and in the infusion line in the respective cases. The known drip chambers are highly reliable in trapping the air bubbles. Nevertheless, there is a risk of air bubbles being infused into the patient intravenously. For a further increase in safety, European Commission Requirement DIN/EN 60601-2-16 sets stringent standards for blood treating apparatus air detectors. The known air detectors are based on the different absorption of ultrasound in liquid and gaseous media and on the scatter of ultrasound at interfaces. As well as the ultrasonic detectors, there are also known air detectors that are based on the different dielectric constants and the different conductivities of liquid and gaseous media. To detect air, signal pulses are coupled into the flowing liquid, and the signal pulses emerging from the flowing liquid are received. It is then determined that air is present when the received signal is below one or more fixed reference levels.

So that the measured results are not falsified, changes in the ambient conditions that affect the received signal have to be compensated for. There are various methods of compensation that are used for this purpose. An arrangement for detecting air bubbles in flowing liquids, which is based on ultrasonic measurement and has compensation for the ambient factors is known from, for example, EP 1182452 A2.

The known methods of monitoring flowing liquids for the presence of air have proved satisfactory in practice for detecting relatively large air bubbles. This is because the relatively large air bubbles, whose volume exceeds approximately 1 µl as individual bubbles and approximately 50 µl as a bolus, cause relatively short and large changes in signal. The ambient factors change relatively slowly by contrast and their effects can therefore easily be detected. In this way, the correction for the ambient factors takes place over a substantially longer period of time than the period occupied by the changes in signal attributable to the air bubbles.

As well as the relatively large individual bubbles, very small bubbles, so-called micro-bubbles, may also occur in hemodialysis treatments. These typically arise when air is able to penetrate into the arterial segment of the extra-corporeal blood circulatory system due to leaks. The individual bubbles, which as a rule are still relatively large at the outset, are first reduced in size by the blood pump. When they then pass through the capillaries of the dialyzer, the inside diameter of which is generally approximately 0.2 mm, they are reduced in size even more. The larger of the small bubbles can be separated out in the venous bubble trap due to their buoyancy whereas the micro-bubbles, which generally have a diameter of approx. 0.2 mm and a volume of approximately 4 µl, are transported out of the bubble trap along with the flow of blood and can travel into the patient. Micro-bubbles having a continuous distribution of diameters and a maximum diameter of approximately 0.3 mm are then present in the patient's bloodstream.

Before a dialysis treatment, the extra-corporeal blood circulatory system is usually flushed out with an isotonic saline solution. In this case, there is a danger that air bubbles which are not flushed free may detach during the treatment and may be infused into the patient undetected in a "cloud" of micro-bubbles.

In the literature (Droste D. W., Kuhne K., Schaefer R. M., Ringelstein B. B; Detection of microemboli in the subclavian vein of patients undergoing haemodialysis and haemodiafiltration using pulsed Doppler ultrasound. *Nephrol. Dial. Transplant* 2002; 17: 462-466), there are indications that micro-embolisms, whose cause is suspected to be the presence of micro-bubbles, typically occur in dialysis treatments. It is true that the human body will tolerate relatively large amounts of air if it is administered intravenously, because the air can be expired in the lungs or dissolved in the blood. In practice, a continuous rate of air infusion of up to 1.5 ml/min is accepted for a body weight of 50 kg and a maximum blood flow-rate of 600 ml/min. If however these limiting values should be exceeded, then there may be serious complications during the treatment of the blood.

SUMMARY OF THE INVENTION

One aspect of the present invention is a method of monitoring a flowing liquid for the presence of air, which allows even relatively small air bubbles, and in particular micro-bubbles, to be detected with high reliability, for the detection of different incidents. A further aspect of the present invention is a method for the extra-corporeal treatment of blood using an extra-corporeal blood circulatory system, by which even relatively small air bubbles, and in particular micro-bubbles, can be detected in the extra-corporeal circulatory system with high reliability.

Another aspect of the present invention is a device for monitoring a flowing liquid for the presence of relatively small air bubbles, and in particular micro-bubbles, and an extra-corporeal blood treatment apparatus having a monitoring arrangement of this kind.

The method of the present invention comprises: coupling a sequence of signal pulses or a continuous signal into the flowing liquid, receiving the signal pulses or the continuous signal emerging from the flowing liquid, and extracting a signal pattern from the signal pulses or continuous signal received that is characteristic of the variation over time, over a preset interval of time, of the signal pulses or continuous signal received. This characteristic signal pattern is then compared with a characteristic reference pattern which is characteristic of an air-free liquid, and it is determined that air is present when the characteristic signal pattern deviates from the characteristic reference pattern by a preset amount. Any of the methods known from pattern recognition can be used for analyzing the received signal.

For the comparison of the signal pattern and reference pattern, the physical form of the signal pulses or the continuous signal is immaterial. Preferably, the signal pulses are pulses of ultrasound and the continuous signal is an ultrasound signal. Alternatively, the signals may be electrical fields or electromagnetic radiation. Alternatively, any signals that are altered by the presence of air in the flowing liquid may be used.

In a defined interval of time $\Delta t$, $\Delta N$ micro-bubbles, which have a continuous distribution of volume, pass through the measurement gap. The presence of micro-bubbles causes a change over time in the received signal, which latter may be in the form of a continuous signal $x(t)$ or a continuous sequence of discrete values $x_i(II)$. The variation over time of the received signal constitutes the characteristic signal pattern $E_{mess,\Delta N}$.

If there are no micro-bubbles present, the received signal shows a characteristic signal pattern and is clearly distinguished from the characteristic signal pattern of the received signal when there are micro-bubbles present. The characteristic signal pattern is determined only by the changes in the ambient factors, which include for example disruptions in the emitter or receiver or fluctuations in the density of the flowing liquid.

The characteristic signal pattern generally represents a signal affected by noise. As the air infusion rate rises, so does the number $\Delta N$ of micro-bubbles, with the distribution of the micro-bubbles generally changing towards larger volumes. This leads to more frequent changes in signal and to changes in the signal amplitude which are in some cases larger. The received pattern changes from an air-free pattern $E_{mess,0}$ (characteristic signal pattern) to an air-charged pattern $E_{mess,\Delta N}$ (characteristic signal pattern).

The characteristic signal pattern $E_{mess,0}$ is laid down as a characteristic reference pattern $E_{ref,0}$ and preferably as a type pattern. It is also possible for the characteristic reference pattern to be re-determined cyclically in operation if it can be ensured that there are no air bubbles present in the measurement gap.

If the characteristic signal pattern differs significantly from the characteristic reference pattern, an alarm state can be generated. In this way, the maximum sensitivity that is possible for the detection of micro-bubbles can be implemented. If, for system-related reasons, a sufficiently clear-cut distinction can be made between the air-free state and the state where the patient is at risk, it is also possible for an alarm state to be triggered only from the point when a preset limiting value is reached.

As well as the air-free characteristic signal pattern $E_{mess,0}$ other reference patterns $E_{ref,\Delta N}$ may also be used as a characteristic reference pattern $E_{ref,0}$ for defined intakes of air to enable a distinction between different events. For example, a reference pattern which is characteristic of a single micro-bubble, or a reference pattern which is characteristic of a superimposition of N micro-bubbles, may be used. This makes it possible for the volume of included air to be determined as an absolute magnitude. A reference pattern that defines the intake of air at which the limiting value for a hazard is reached may also be used.

The preset interval of time over which the variation over time of the received signal pulses or the continuous signal is assessed can be selected to be so small that the relatively slow changes caused by the ambient factors can be considered to be constant. If this is the case, then any compensation for the changes caused by the ambient factors can be abandoned.

It is advantageous if the interval of time $\Delta t$ is matched to the order of magnitude of the transit time of the micro-bubbles through the measurement gap. It is also advantageous if the interval of time $\Delta t$ is preset as a function of the blood flow-rate.

In a preferred embodiment of the method and device according to the present invention, the variation over time of the signal pattern and reference pattern are not directly compared with one another. Rather one or more characteristic parameters, which are characteristic of their variation over time, is determined from the signal pattern and the reference pattern. These characteristic parameters are then compared with one another. One or more defined parameters are generally sufficient for the characteristic reference pattern.

Due to the nature of a stream of micro-bubbles, it is not possible, even with a constant intake of air, for an exact prediction to be made of how many micro-bubbles $\Delta N$ will pass through the measurement gap during the interval of time $\Delta t$ and what the frequency distribution of the volumes of these $\Delta N$ micro-bubbles will be. The characteristic signal pattern may, however, be seen as the result of a stochastic process and may advantageously be assessed with relatively little cost and effort by using the algorithms for the statistical analysis of time series. The assessment may be made on the basis of a frequency distribution in the time domain or on the basis of a spectral analysis of stochastic processes.

Where frequency distribution in the time domain is assessed, the received signal is seen as a one-dimensional random variable X, in which case its realizations x may cover a discrete or continuous range of values. The statistical properties of the random variable are fully defined by its distribution function $F(x)$ or by the continuous distribution density function $f(x)$ or by the discrete probabilities $w_i$.

To reduce the cost and effort, it is advantageous for the distribution functions $F(x)$ which are determined and compared with one another not to be the complete ones but for them to be confined to one or more characteristic attributes. These meaningful characteristic values are usually defined as expected values of a function $g(x)$ by:

$$E(g(X)) = \int_{-\infty}^{\infty} g(x)f(x)dx \qquad (1.1a)$$

$$E(g(X)) = \sum_i g(x_i)w_i \qquad (1.1b)$$

Equation (1.1a) applies when there is a continuous random variable X and equation (1.1b) applies when the random variable X is discrete, $w_i$ being the probability of the realization of $x_i$.

There is a further advantageous simplification if the mean value $E(X)$ in the following equations is calculated not from the data relating to the present interval of time $\Delta t$ but from that for previous intervals. This generally produces additional errors of an acceptable size if the interval of time $\Delta t$ is selected to be sufficiently small for the typical change in the mean value over time to be negligible.

Advantageous parameters are:
1. Mean value:

$$g(X)=X \qquad (1.2)$$

2. Scatter or variance $\sigma^2$ or standard deviation $\sigma$:

$$g(X)=(X-E(X))^2 \qquad (1.3)$$

3. Moments of $k^{th}$ order:

$$g(X)=X^k \qquad (1.4)$$

4. Absolute moments of $k^{th}$ order:

$$g(X)=|X|^k \qquad (1.5)$$

5. Moments of $k^{th}$ order relative to c:

$$g(X)=(X-c)^k \qquad (1.6)$$

6. Centered moments of $k^{th}$ order:

$$g(X)=(X-E(X))^k \qquad (1.7)$$

7. Absolute centered moments of $k^{th}$ order:

$$g(X)=|X-E(X)|^k \qquad (1.8)$$

8. Skew of the distribution of X
9. Excess of the distribution of X
10. Auto-correlation function: the correlation mean relates to a random process X The following parameters are of importance for two-dimensional random variables. A reference pattern $E_{ref,\Delta N}$ can, for example, be seen as a realization of the random variable $X_1$ and a pattern $E_{mess}$ currently measured can be seen, for example, as a realization of the random variable $X_2$.

11. Co-variance:

$$g(X)=(X_1-E(X_1))(X_2-E(X_2)) \qquad (1.9)$$

12. Correlation coefficient:

$$g(X)=(X_1-E(X_1))/\sigma_1(X_2-E(X_2))/\sigma_2 \qquad (1.10)$$

13. Cross-correlation function: the correlation mean relates to two different random processes $X_1$, $X_2$.

As well as frequency distribution being assessed in the time domain, spectral analysis may also be used to determine one or more parameters from the signal patterns. The aim of spectral analysis (Fourier analysis) is to break down a complex time series having cyclic components into a small number of basic harmonic functions of given frequencies, in which case the time series can be seen as a realization of a one-dimensional random variable X. For the analysis of the received signal, the only frequency ranges in the spectrum that are relevant are the ones that are altered by micro-bubbles. The signal components of relatively high frequency caused by received interference or by electronic noise can be eliminated in this case by filter functions. The signal components of relatively low frequency caused by the change in ambient factors may likewise be blacked out.

Advantageous parameters are:
1. A periodogram (sum of the squares of amplitudes at given frequencies, of the line spectrum type)
2. Spectral density function (energy density spectrum or power density spectrum for given frequencies)
3. Use of filters (smoothing within spectral windows)

When the signal patterns are being compared, it may be of advantage for a plurality of parameters to be combined with one another to increase the sharpness of the distinctions that can be made when detecting micro-bubbles. It is, for example, possible for the conclusion to be reached that an incident has occurred if two parameters have undergone a given change but there has been no significant change in a third parameter.

Variance (standard deviation, scatter) has proved to be particularly advantageous as a characteristic parameter. Variance is a metric indicating how the individual items of data are distributed about the mean value, i.e. how great the scatter of the items of data is about the mean value. Given that variance is a parameter from which the mean value is purged, the ambient factors are eliminated, because the change in the absolute signal amplitude, such for example as in the mean value of the signal, over the interval of time $\Delta t$ is not assessed as a change in the pattern.

In a further preferred embodiment of the method and device according to the present invention, characteristic signal patterns are determined continuously in a sequence of intervals of time and are each compared with one or more reference patterns. An alarm can be given if one of the characteristic signal patterns differs by a preset amount from the characteristic reference pattern. It is also possible for an alarm to be given only when a difference by a preset amount is found in a given number of intervals of time. The number of events where a difference is found is counted during the treatment of the blood. The number of events in this case is a measure of the total volume of air contained in the liquid.

In a further preferred embodiment, a sequence of signal pulses, rather than one continuous signal, is coupled into the flowing liquid, and a characteristic signal pattern is the maximum amplitudes of the received signal pulses in a preset period of time. Alternatively, any of the parameters that correlate with the signal amplitude may be determined in place of the maximum signal amplitude.

BRIEF DESCRIPTION OF THE DRAWINGS

A preferred embodiment of the present invention is explained in detail below by reference to the drawings.

DETAILED DESCRIPTION OF THE DRAWINGS

Figure 1:
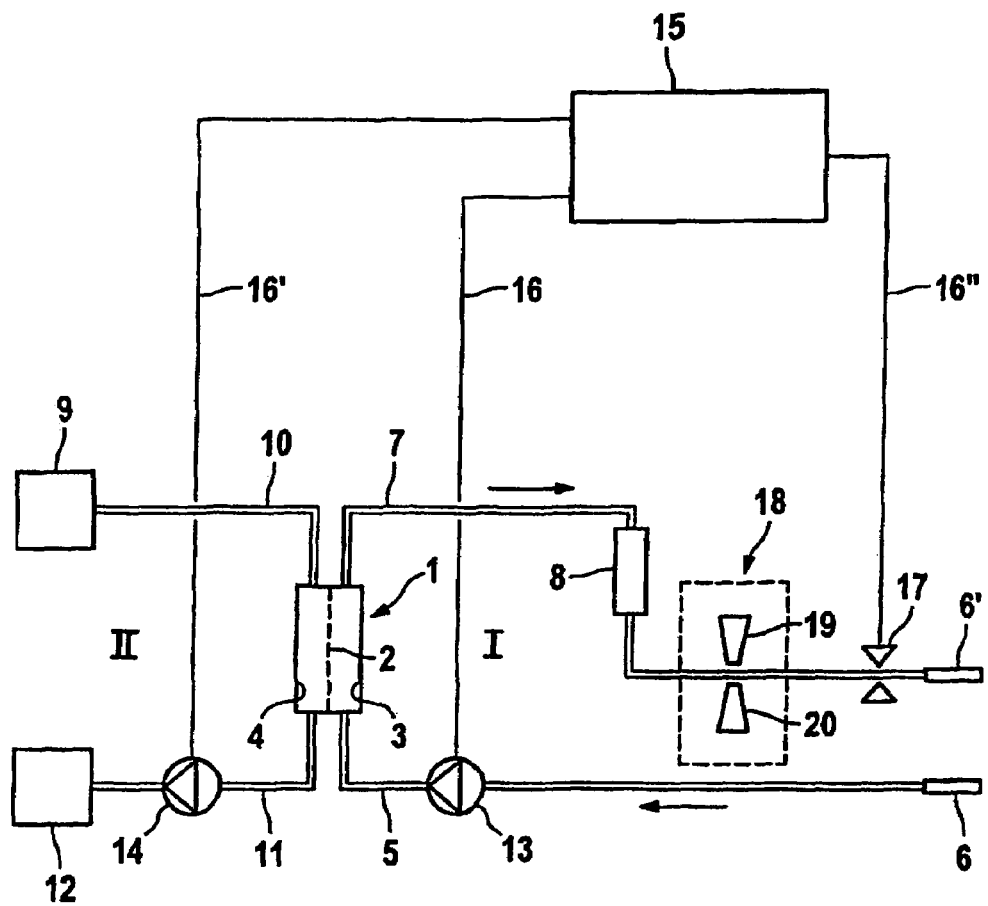
FIG. 1 is a simplified schematic representation of the principal components of an apparatus for treating blood, having an extra-corporeal blood circulatory system together with a device for monitoring the blood flowing in the circulatory system for the presence of air.

FIG. 1 shows the principal components of the apparatus for treating blood together with the monitoring arrangement. The apparatus for treating blood, such as a hemodialysis apparatus for example, has a dialyzer 1 which is divided by a semi-permeable membrane 2 into a blood chamber 3 and a dialysis liquid chamber 4. The inlet to the blood chamber is connected to one end of the blood supply line 5, while the outlet from the blood chamber 3 is connected to one end of a blood takeaway line 7, into which a drip chamber 8 is connected. The other ends of the blood supply and takeaway lines 5, 7 are connected to arterial and venous needles 6 and 6' respectively.

Arranged on the blood takeaway line 7 between the drip chamber 8 and the venous needle 6' is an electromagnetically actuatable venous tube clamp 17. Together with the blood chamber 3, the blood supply and takeaway lines 5, 7 constitute the extra-corporeal blood circulatory system I of the hemodialysis apparatus.

The dialysis liquid system II of the dialysis apparatus comprises a means 9 for processing the dialysis liquid, from which runs a dialysis liquid supply line 10 which goes to the dialysis liquid chamber 4 of the dialyzer 1. A dialysis liquid takeaway line 11, which goes to an outlet 12, runs from the dialysis liquid chamber 4.

Arranged in the blood supply line 5 is a blood pump 13, while in the dialysis liquid takeaway line 11 there is arranged a dialysis liquid pump 14. During the treatment of the blood, the blood pump 13 and dialysis liquid pump 14 respectively pump blood through the extra-corporeal blood circulatory system I and dialysis liquid through the dialysis liquid system II.

The hemodialysis apparatus comprises a central control unit 15 which is connected via control lines 16, 16' and 16" to the blood pump 13, the dialysis liquid pump 14 and the tube clamp 17 respectively.

The hemodialysis apparatus also has an arrangement for monitoring the blood flowing in the extra-corporeal blood circulatory system I for the presence of air. In the case of the apparatus described, this monitoring arrangement is part of the hemodialysis apparatus, but it may equally well be a separate sub-assembly.

Figure 2:
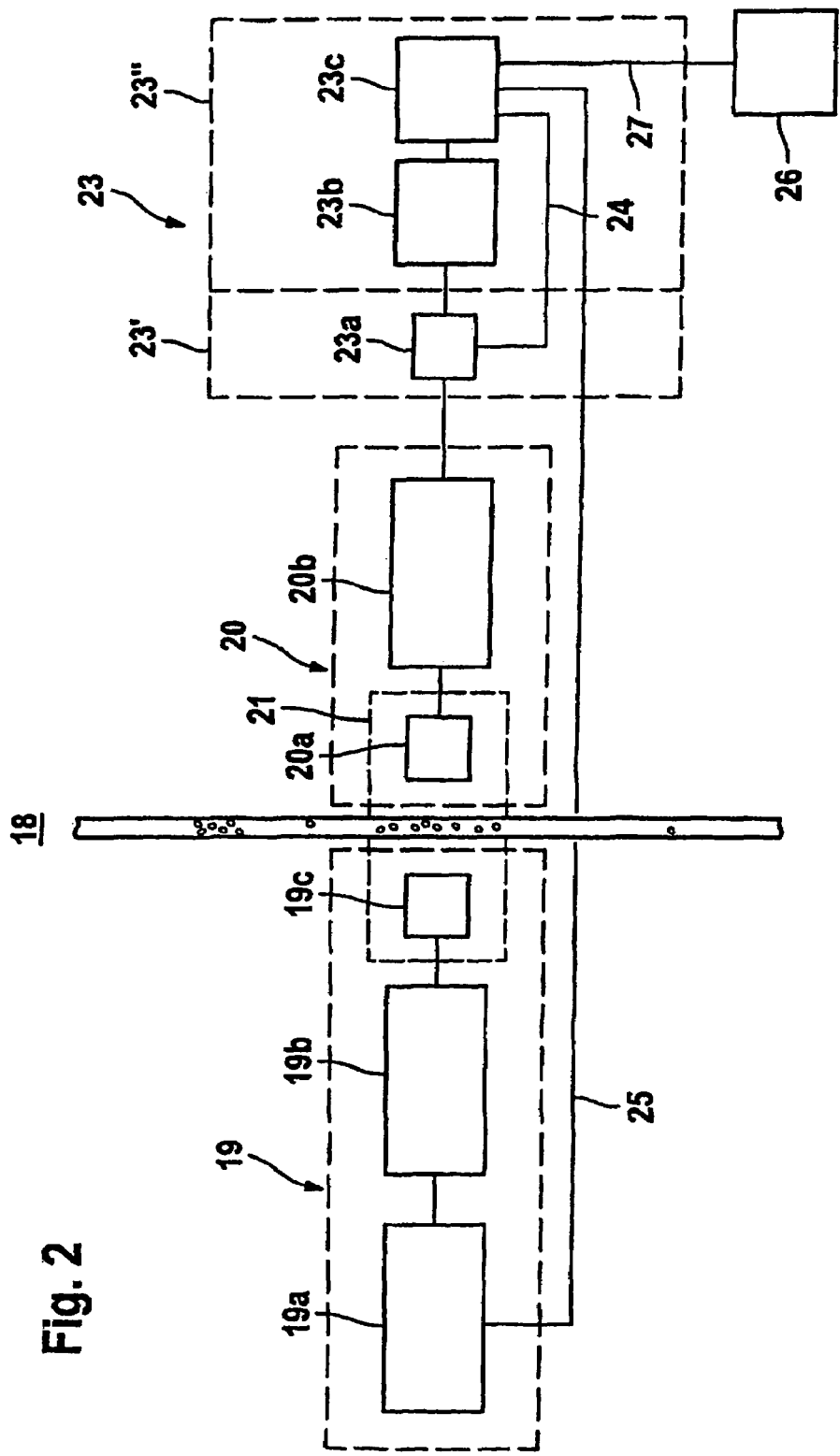
FIG. 2 is a schematic representation of the principal components of an embodiment of the device for monitoring the blood for the presence of air.

The monitoring arrangement 18 is only schematically indicated in FIG. 1. The individual components of the monitoring arrangement are shown in FIG. 2. The monitoring arrangement 18 has an ultrasonic emitter 19 and an ultrasonic receiver 20. The ultrasonic emitter 19 has a pulse generator 19a and a power stage 19b and an ultrasonic transducer 19c, while the ultrasonic receiver has an ultrasonic transducer 20a and a signal amplifier 20b. The ultrasonic transducer 19c of the emitter 19 and the ultrasonic transducer 20a of the receiver 20 are arranged parallel to one another, on the two sides of the blood takeaway line 7, downstream of the drip chamber 8 and upstream of the tube clamp 17, on a sensor carrier 21 in such a way that the blood flowing in the blood takeaway line 7 has ultrasound transmitted through it orthogonally. The two ultrasonic transducers 19c and 20a may be discs of piezo-electric ceramic material. The space between the two transducers forms an acoustic measurement gap.

The ultrasonic emitter 19 operates in the pulsed mode. For this purpose, the pulse generator 19a is driven cyclically by a microcontroller 23c, which is responsible for controlling the sequence and for signal analysis and which is connected to the pulse generator 19a by a signal line 25. The pulse generator 19a then generates electrical signals which are fed via the power stage 19b to the ultrasonic transducer 19c.

The ultrasonic transducer 20a of the receiver 20 converts the ultrasonic signals back into electrical signals, which are fed to the signal amplifier 20b. The signal amplifier 20b filters and processes the electrical signal in such a way that it can be fed to an analyzing unit 23.

The analyzing unit 23 has means 23' for extracting a signal pattern which is characteristic of the variation over time of the ultrasonic pulses received, and means 23" for comparing the characteristic signal pattern with a reference pattern.

The means 23' for extracting the signal pattern has a peak detector 23a which determines the maximum signal amplitude of the pulses as a measure of the level of the ultrasonic pulses received by the ultrasonic transducer 20a, while the means 23" for comparing the characteristic signal pattern with a reference pattern has an A/D converter 23b and the microcontroller 23c.

The analogue voltage value supplied by the peak detector 23a is converted by the A/D converter 23b into a digital value for further signal processing. Before each ultrasonic pulse is emitted by the ultrasonic transducer 19c, the peak detector 23a is reset by the microcontroller 23c, which is connected to the peak detector 23a by a signal line 24. Hence there is present at the output of the peak detector 23a a signal pattern that is characteristic of the variation over time of the received ultrasonic pulses during a preset interval of time $\Delta t$. In the embodiment, the preset interval of time $\Delta t$ covers a total of m=128 values, each value representing the maximum amplitude of the ultrasonic pulse received.

Due to the constant excitation of the ultrasonic transducer 19c of the emitter 19, changes in the acoustic properties of the measurement gap are reflected in the magnitude of the maximum amplitude of the analogue signal supplied by the peak detector 23a and in the size of the digital signal present at the A/D converter.

The acoustic properties of the measurement gap change when un-dissolved air in, for example, the form of tiny individual bubbles of air, i.e. micro-bubbles, is present in the blood flowing through the blood takeaway line 7. The micro-bubbles in the acoustic measurement gap cause the ultrasonic pulses to be attenuated and hence a dip to occur in the maximum amplitude. The variation in the maximum amplitude, which can be measured over time, is thus subject to a modulation corresponding to the attenuation which is operative at the time in the acoustic measurement gap.

Figure 3:
FIG. 3 shows the variation over time of the characteristic reference pattern when there are no air bubbles present in the flowing liquid.

If there are no micro-bubbles present in the blood, no significant dips can be seen in the signal amplitude. FIG. 3 shows a signal pattern of this kind that is used as a characteristic reference pattern. All that can be seen are tiny changes in signal (noise) which are of a relatively high frequency.

Figure 4A:
FIG. 4a shows the variation over time of the characteristic reference pattern when there are a large number of air bubbles present in the liquid.
Figure 4B:
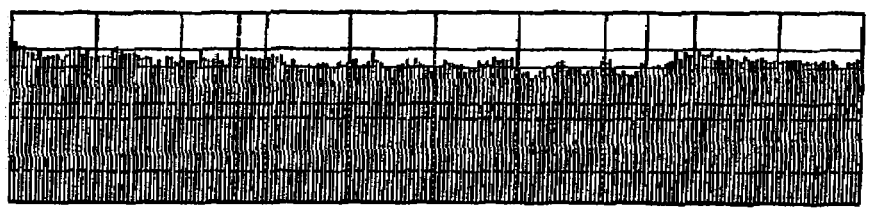
FIG. 4b shows details of the signal pattern from FIG. 4a in an enlarged scale.

FIGS. 4a and 4b show a signal pattern which is characteristic of the presence of a large number of micro-bubbles. The dips in signal amplitude can clearly be seen. The signal pattern shown in FIG. 4a covers a plurality of successive intervals of time $\Delta t$. The variation over time of the signal pattern for one of the intervals of time $\Delta t$ is shown to an enlarged scale in FIG. 4b. The relatively large changes in the signal, which are however of relatively low frequency, are typical. The interval of time $\Delta t$ covers m=128 values.

Figure 5A:
FIG. 5a shows the variation over time of the characteristic signal pattern when there are few air bubbles present in the liquid.
Figure 5B:
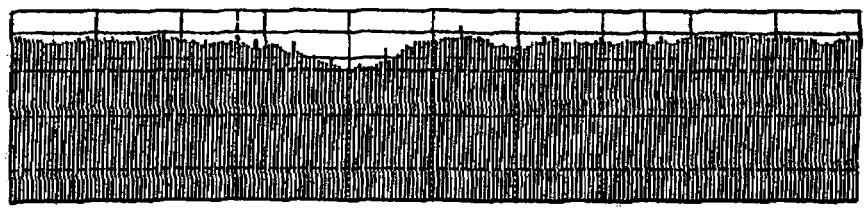
FIG. 5b shows details of the signal pattern from FIG. 5a in an enlarged scale.

FIGS. 5a and 5b show signal patterns which are characteristic of the presence of few micro-bubbles. If the signal patterns in FIGS. 4a, 4b and FIGS. 5a, 5b are compared, it can be seen that considerably fewer dips in signal amplitude are apparent in the signal pattern shown in FIGS. 5a, 5b.

To enable the characteristic signal pattern to be compared with the reference pattern, a characteristic statistical parameter is determined, from the signal pattern, for each of the successive intervals of time in the analyzing unit 23, which is part of the microcontroller 23c. In this embodiment, the characteristic statistical parameter is the variance $\sigma^2$ of the signal pattern. Because variance is an attribute where, by definition, the measured values are purged of the mean value, the effect of the ambient conditions is suppressed.

Variance is calculated from equations 1.1b and 1.3. A constant value is inserted in equation 1.1b for the probabilities $w_i$. Because the basis for the data is a random sample and not a complete population, the normalization condition and the need for unbiasedness result in the value in question being $w_i=1/(m-1)$, where the pattern covers m=128 values.

The mean E(x) is not calculated in the equations in this case from the data for the interval of time $\Delta t$ in which the analysis is currently being made, and instead use is made of the mean that was determined in one or more of the preceding intervals of time. For this method, however, the interval of time Δt selected must be so small that changes in the mean can be ignored.

In this embodiment, the variance is also not calculated from the characteristic reference pattern shown in FIG. 3. It is enough to set, as the variance for the reference pattern, a limiting value at which it is assumed that there will be a hazard to the patient if the value is exceeded.

The variance $\sigma^2$ of the characteristic signal pattern is then compared with the preset limiting value in the analyzing unit 23. If the variance $\sigma^2$ is higher than the limiting value, it is concluded that micro-bubbles are present during the preset interval of time Δt. Comparison with a plurality of limiting values enables a distinction to be made between the presence of few, or many, air bubbles.

In the event of a volume of bubbles which constitutes a hazard to the patient being detected in a preset interval of time, the analyzing unit 23 generates an alarm signal, that is received by an alarm unit 26 which is connected by a control line 27 to the analyzing unit 23. The alarm unit 26 then generates an acoustic and/or visual alarm. At the same time, the alarm unit 26 also generates a control signal that is applied to the control unit 15 of the dialysis apparatus via a signal line which is not shown. If this control signal is generated, the control unit 15 suspends the dialysis treatment by stopping the blood pump 13 and actuating the tube clamp 17 to clamp off the blood takeaway line 7.

In an alternative embodiment, provision is made for an alarm to be given only if micro-bubbles are detected in a plurality of intervals of time.

In the event of the analyzing unit 23 detecting micro-bubbles in one of the intervals of time Δt, the said analyzing unit 23 generates a count signal. During the treatment of the blood or during a continuous or discontinuous sequence of intervals of time, the number of count signals generated by the analyzing units 23 is counted at the successive measurements. During the dialysis treatment, the number of count signals is continuously compared with a further preset limiting value. If the count reaches the limiting value, the analyzing unit 23 once again generates an alarm signal so that the alarm unit 26 will emit an acoustic and/or visual alarm and the control unit 15 will suspend the treatment of the blood. It is assumed in this case that the total volume of air contained in the blood constitutes a hazard to the patient.

The invention claimed is:

1. A method of monitoring a flowing medium for the presence of air comprising:
   coupling of a sequence of signal pulses or a continuous signal into the flowing medium;
   receiving the signal pulses or the continuous signal from the flowing medium;
   extracting a signal pattern over a time interval that is characteristic of the variation over time of the signal pulses or the continuous signal received;
   comparing the signal pattern with one or more reference patterns comprising:
      determining one or more statistical parameters from the signal pattern; and
      comparing the one or more statistical parameters with one or more statistical reference parameters, wherein a first statistical parameter is variance; and
   determining that air is present in the flowing medium if the signal pattern differs from the one or more reference patterns by a preset amount.

2. The method of claim 1, further comprising:
   continuously extracting the signal pattern in a sequence of time intervals; and
   comparing each signal pattern with one or more reference patterns.

3. The method of claim 2, further comprising:
   calculating the mean in a preceding time interval.

4. The method of claim 1, further comprising:
   determining the maximum signal amplitudes of the signal pulses received, wherein the signal pattern is the sequence of maximum amplitudes of the signal pulses that occurs during a preset interval of time.

5. The method of claim 1, wherein the sequence of signal pulses or the continuous signal is a sequence of ultrasonic pulses or a continuous ultrasonic signal, respectively.

6. The method of claim 1 wherein the flowing medium is blood in an extra-corporeal blood circulatory system.

7. A system for monitoring a flowing medium for the presence of air comprising:
   means for coupling a sequence of signal pulses or a continuous signal into the flowing medium;
   means for receiving the signal pulses or continuous signal emerging from the flowing medium; and
   an analyzing unit comprising:
      means for extracting a signal pattern over a time interval that is characteristic of the variation over time of the signal pulses or the continuous signal received;
      means for comparing the signal pattern with one or more reference patterns to determine that air is present if the signal pattern differs from the one or more reference pattern by a preset amount comprising: a means for determining one or more statistical parameters from the signal pattern and comparing the statistical parameters with one or more statistical reference parameters, wherein one of the one or more statistical parameters is variance.

8. The system of claim 7, wherein the means for extracting a signal pattern further comprises:
   means for continuously extracting the signal pattern in a sequence of time intervals and comparing each signal pattern with one or more reference patterns.

9. The system of claim 8, further comprising:
   means for calculating the mean in a preceding time interval.

10. The system of claim 7, further comprising:
    means for determining the maximum signal amplitudes of the signal pulses received, wherein the signal pattern is the sequence of maximum amplitudes of the signal pulses that occurs during a preset interval of time.

11. The system of claim 7, wherein the means for emitting is an ultrasonic emitter and the means for receiving is an ultrasonic receiver.

12. A system for monitoring the presence of air in blood in an extra-corporeal blood circulatory system comprising:
    an ultrasonic emitter for coupling a sequence of signal pulses or a continuous signal into the flowing medium;
    an ultrasonic receiver for receiving the signal pulses or continuous signal emerging from the flowing medium; and
    an analyzing unit comprising:
    a detector for extracting a signal pattern over a time interval that is characteristic of the variation over time of the signal pulses or the continuous signal received; and
    a microcontroller for comparing the signal pattern with one or more reference patterns to determine that air is present if the signal pattern differs from the one or more reference pattern by a preset amount, wherein said analyzing unit is adapted to determine one or more statistical parameters from the signal pattern and compare the statistical parameters with one or more statistical reference parameters, wherein one of the one of more statistical parameters is variance.

13. The method of claim 1, wherein one or more statistical parameter comprises two statistical parameters, and one or more statistical reference parameters comprises two reference parameters.

14. The method of claim 1, wherein one or more statistical parameter comprises three statistical parameters, and one or more statistical reference parameters comprises three reference parameters.

15. The method of claim 13, wherein the second statistical parameter is a periodogram or a spectral density function.

16. The method of claim 13, wherein if air is determined to be present, an alarm is triggered.

* * * * *